United States Patent [19]
Kurz et al.

[11] 3,966,964
[45] June 29, 1976

[54] VETERINARY COMPOSITION CONTAINING THIONOSALICYLIC ACID ANILIDES OR SALTS THEREOF AND METHODS OF USING THE SAME

[75] Inventors: Jurgen Kurz, Wuppertal-Elberfeld; Heinrich Kolling, Hannover, Rhineland; Manfred Federmann, Wuppertal-Elberfeld, all of Germany

[73] Assignee: Bayer Aktiengesellschaft, Germany

[22] Filed: Feb. 13, 1975

[21] Appl. No.: 549,689

Related U.S. Application Data

[60] Division of Ser. No. 861,158, Sept. 25, 1969, Pat. No. 3,898,272, which is a continuation-in-part of Ser. No. 634,835, May 1, 1967, abandoned.

[30] Foreign Application Priority Data

| May 6, 1966 | Germany | 49138 |
| Aug. 17, 1966 | Germany | 49965 |
| Sept. 3, 1966 | Germany | 50110 |

[52] U.S. Cl. ............................ 424/308; 424/311; 424/324
[51] Int. Cl.² ........................................ A61K 31/235
[58] Field of Search .................. 424/308, 311, 324

[56] References Cited
UNITED STATES PATENTS

| 2,703,332 | 3/1955 | Bindler et al. | 424/233 |
| 2,731,386 | 1/1956 | Reiner | 424/231 |
| 3,714,231 | 1/1973 | Kolling et al. | 424/308 |

*Primary Examiner*—V. D. Turner

[57] ABSTRACT

New thionosalicylic acid anilides and salts with bases are provided which have parasiticidal activity in sheep and cattle particularly against adult liver flukes in sheep and cattle and other domestic animals, especially against juvenile liver flukes. The new compounds are produced by the reaction of poly-substituted phenols with substituted aromatic isothiocyanates, the hydrolysis products of oxo-thiono- or dithiono-dihydrobenzoxazines or by the reaction of N-phenyl-salicyl-imide chlorides with thio-compounds. Typical compounds are 3,5-dichloro-4'-bromo-thionosalicylic acid anilide and 2-acetoxy-3,5-dichloro-N-(2'-methyl-4'-chlorophenyl)-thionobenzamide. Novel benzoxazines obtainable from the above anilides are also provided and have similar properties. Typical compounds are 3-(3',5'-bis-trifluoromethyl-phenyl)-6,8-dibromo-2-oxo-4-thiono-dihydrobenzoxazine-(1,3), 3-(3',4'-dichlorophenyl)-6,8-dichloro-2,4-dithiono-dihydrobenzoxazine-(1,3) and 3-(4'-bromophenyl)-6-chloro-8-bromo-2,4-dithiono-dihydrobenzoxazine-(1,3). Methods for preparing a large number of both types of compounds are described. The compounds are administered orally or subcutaneously in doses of 2.5 to 100 mg/kg, preferably 5 to 15 mg/kg, of body weight.

52 Claims, No Drawings

VETERINARY COMPOSITION CONTAINING THIONOSALICYLIC ACID ANILIDES OR SALTS THEREOF AND METHODS OF USING THE SAME

This is a division of our copending application Ser. No. 861,158, filed Sept. 25, 1969 now U.S. Pat. No. 3,898,272 issued Aug. 5, 1975, which is in turn a continuation-in-part of our then copending application Ser. No. 634,835, filed May 1, 1967, now abandoned.

PRIOR ART

Some thionosalicylic acid anilides substituted in the aromatic nucleus of the acid component are known. (cf. H. Rivier, S. Kunz, Helv. Chim. Acta 15 (1932), 376; E. Schraufstätter, W. Meiser, R. Gonnert, Z. Naturforsch. 16 b (1961), 95; G. Wagner, D. Singer, Z. Chemie 3 (1963), 146; German Pat. No. 1,045,717). These known compounds, however, are ineffective against trematodes, especially against liver flukes, for example *Fasciola hepatica*.

It has now been found according to the present invention that certain novel thionosalicylic acid anilides and salts thereof with suitable bases have valuable veterinary chemotherapeutic and biological parasiticidal properties. The invention also includes novel parasiticidal dihydrobenzoxazines and procedure for producing said anilides and benzoxazines.

The new thionosalicylic acid anilides of this invention have the formula:

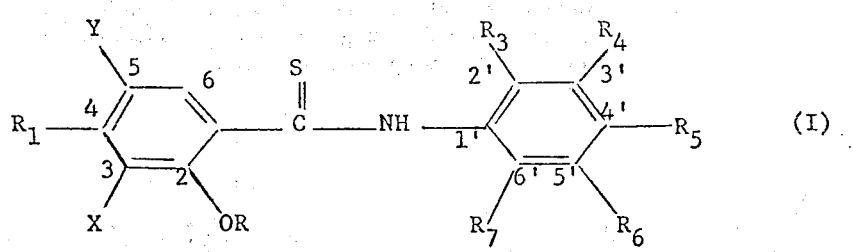

(I)

wherein
R is hydrogen, lower akyl carbamoyl, alkyl carbonyl, monocyclic lower aralkyl carbonyl or lower alkane-sulphonyl.
$R_1$ is hydrogen or lower alkyl.
$R_3$, $R_4$, $R_5$, $R_6$ and $R_7$ are the same or different and are each hydrogen, lower alkyl, lower alkoxy, halogen, nitro, hydroxy, trifluoromethyl or lower alkylmercapto and
X and Y are the same or different and are each hydrogen, halogen or nitro,
with the provisos that X and Y cannot both be hydrogen at the same time and in the case where X, $R_1$ and $R_3$ to $R_7$ are all hydrogen Y cannot be halogen, and when $R_5$ is halogen or nitro and X and $R_1$, $R_3$, $R_4$, $R_6$ and $R_7$ are all hydrogen Y cannot be halogen and when $R_4$ and $R_6$ are both halogen and X, $R_1$, $R_3$, $R_5$ and $R_7$ are all hydrogen Y cannot be halogen.

A particularly valuable group of the new thionosalicylic acid anilides is those in which R in the above formula (I) is acyl, namely, compounds of the formula:

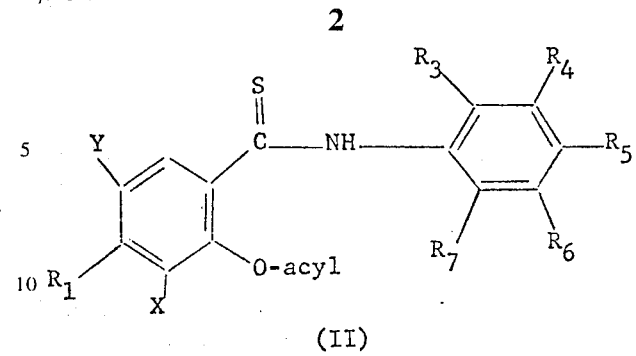

(II)

wherein $R_1$, $R_3$, $R_4$, $R_5$, $R_6$, $R_7$, X and Y have the same meanings set forth above and with the same provisos. Compounds in which R is acetyl, propionyl, phenylpropionyl, pivaloyl, etc., are especially active.

The new compounds of formula (I) and their salts with non-toxic inorganic or organic bases, such as sodium hydroxide and potassium hydroxide, ethanolamine, diethanolamine, piperazine, etc., and the compounds of formula (II) destroy internal parasites including cestodes and trematodes and of the latter particularly the liver flukes. They are also active antibacterial, antifungal and antiprotozoan agents and have, for example, good bactericidal, nematocidal and molluscicidal effects and are active against homo- and phytopathogenic fungi such as *Trichophyton mentagrophytes*, *microsporium felineum*, *Aspergillus niger*, *Penicillium commune*, etc. The compounds (I), (II) show particularly good activity against snails and worms, especially against liver flukes (*Fasciola hepatica*) and also against bacteria, fungi and protozoa, for example coccidia. They are administered in oral dosage forms with the usual excipients or subcutaneously in solution or suspension form at dosages of 2.5 to 100 mg/kg, preferably 5 to 15 mg/kg, of body weight depending on the particular compound being used.

The new compounds (I) are prepared by reacting a substituted phenol of the formula:

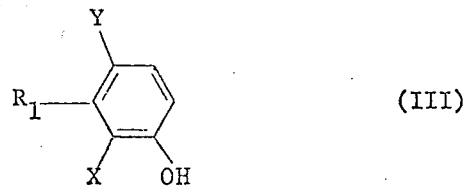

(III)

with a substituted aromatic isothiocyanate of the formula:

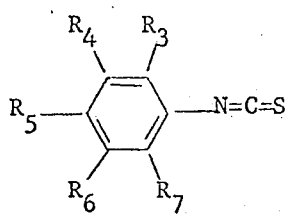  (IV)

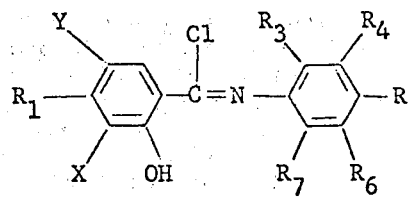  (VII)

in per se known manner in the presence of a Friedel-Crafts-catalyst, and acylating, when desired, the reaction products with a lower alkylisocyanate or an acid chloride of the formula:

R'—Cl  (VI)

wherein $R_1$, $R_3$ to $R_7$, X and Y are as above defined and R' is alkyl carbonyl, monocyclic lower aralkyl carbonyl or lower alkanesulphonyl.

The compounds (I) are also obtained by hydrolyzing, in per se known manner, 2-oxo-4-thiono-dihydro-benzoxazines-(1,3) and/or 2,4-dithiono-dihydro-benzoxazines-(1,3) of the formula:

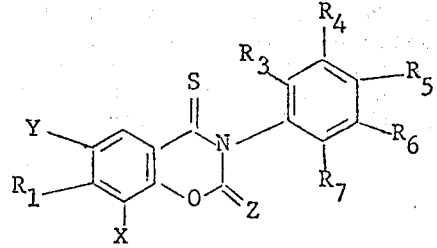  (V)

wherein $R_1$, $R_3$ to $R_7$, X and Y are as above defined, with a thio compound or alkali metal or alkaline earth metal salt thereof of the formula:

HS — $R_8$  (VIII)

in which $R_8$ is hydrogen or an alkali metal or alkaline earth metal or a radical which can easily be detached by hydrolytic splitting of the S—$R_8$-bond, such as

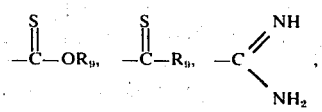

—$SO_3H$, etc., in which $R_9$ is a lower alkyl radical, in a suitable solvent, such as acetone, tetrahydrofuran or dioxan, and hydrolyzing the reaction product according to the following reaction scheme:

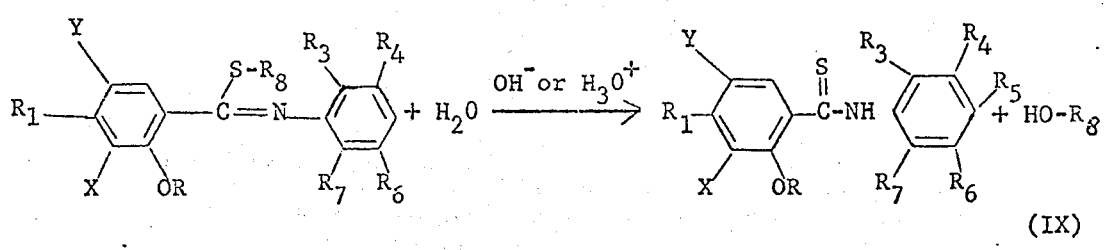  (IX)

in which Z is oxygen or sulphur, and acylating, when desired, the hydrolysis products with a lower alkylisocyanate or an acid chloride of the formula:

R'—Cl  (VI)

wherein $R_1$, $R_3$ to $R_7$, X and Y are as above defined and R' is alkyl carbonyl, monocyclic lower aralkyl carbonyl or lower alkane sulphonyl.

The hydrolysis reaction of the 2-oxo-4-thio-3-phenyl- and/or 2-4-dithio-3-phenyl-dihydrobenzoxazine-(1,3) (V) is carried out in a manner per se known (G. Wagner and W. Singer, Z. Chem. 3, 148 (1963)) by heating a 10 % solution in an inert, water miscible solution medium, such as dioxan, boiling between 50° and 110°C at boiling temperature and introducing 1N caustic, for example, KOH or NaOH.

The compounds (I) can also be obtained by reacting an N-phenyl-salicylimide chloride of the formula:

and acylating, when desired, the hydrolysis products with a lower alkyl isocyanate or an acid chloride of the formula:

R'—Cl  (VI)

wherein $R_1$, $R_3$ to $R_7$, X and Y are as above defined and R' is alkyl carbonyl, monocyclic lower aralkyl carbonyl and lower alkanesulphonyl.

Those N-phenyl-salicylimide chlorides (VII) of the above formula, which are not already known, can be prepared according to known types of methods by reacting the appropriately substituted salicylic acid anilide with thionyl chloride, without or with a suitable solvent, such as benzene, toluene, xylene, etc., and with or without the use of dimethylformamide as catalyst (cf. R. Gonnert. J. Johannis, E. Schraufstätter, R. Strufe, Medizin und Chemie, Verlag GmbH. Weinheim/Bergstrasse 1963, 540; U.S. Pat. No. 3,210,422).

While 3-[4'-bromophenyl]-2-oxo-4-thio-6-bromo-dihydrobenzoxazine-(1,3) known from the publication of G. Wagner and co-workers [Z.Chem. 3, 148 (1963); Pharmazie 21, 161 (1966)] is inactive, the compounds of formula (V) which are used as starting materials exhibit activity against liver flukes such as Fasciola hepatica. These compounds are derivatives of 3-phenyl-2-oxo-4-thio- and 3-phenyl-8c 2,4-dithio-dihydrobenzoxazine-(1,3) and are prepared from the reaction of a compound of formula (I) with a compound of the formula:

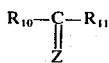  (X)

in which Z is as above defined and $R_{10}$ and $R_{11}$ are identical or different and are halogen, lower alkoxy or lower alkylmercapto groups, or with oxalyl chloride under liberation of 1 mol of CO and 2 mols of HCl, in an inert solvent medium, such as benzol, toluol, xylol, etc. at temperatures preferably between 0° C and the boiling temperature, or by reacting with $P_2S_5$ a compound of the formula:

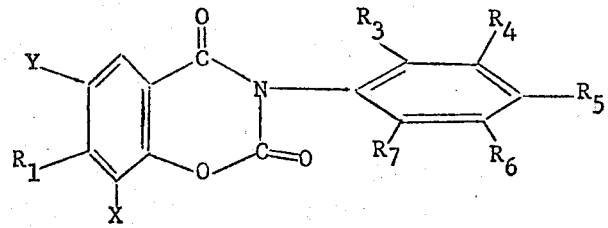

wherein $R_1$, $R_3$ to $R_7$, X and Y are as above defined.

The invention is illustrated by the following non-limitative examples.

EXAMPLE 1

3,5,4'-trichloro-thionosalicylic acid anilide 14.7 Grams (0.045 mole) of N-(4'-chlorophenyl)-3,5-dichlorosalicylic acid imide chloride are dissolved in as little dioxane as possible. A saturated solution of 15.8 g (0.65 mole) of crystallized sodium sulphide in water is rapidly added with vigorous stirring. The mixture is stirred at room temperature for a further 2 hours, then poured into twice its volume of water and acidified with dilute hydrochloric acid. The precipitate is filtered off, washed with water, dried and recrystallized from ligroin. M.p. 142°C.

The following compounds are prepared in analogous manner:

EXAMPLE 2

From N-(2'-chloro-(4'-nitrophenyl)-5-chlorosalicylic acid imide chloride there is obtained 5,2'-dichloro-4'-nitro-thionosalicylic acid anilide, m.p. 148°C.

EXAMPLE 3

From N-(2'-methyl-4'-nitro-5'-chlorophenyl)-5-chlorosalicylic acide imide chloride there is obtained 5,5'-dichloro-2'-methyl-4'-nitro-thionosalicylic acid anilide, m.p. 169°C.

EXAMPLE 4

3,5,2',4',5'-pentachloro-thionosalicylic acid anilide

A solution of 26 g (0.065 mole) of N-(2',4',5'-tri-chlorophenyl)-3,5-dichlorosalicylic acid imide chloride and 13.6 g (0.085 mole) of potassium ethyl zanthogenate in 500 ml of anhydrous acetone is heated at boiling temperature for 4 hours. The mixture is then filtered hot and the solvent removed from the filtrate in a vacuum. The residue is heated with 500 ml of a 10% sodium carbonate solution on a water bath for 1 hour. The mixture is then filtered and the filtrate acidified with dilute hydrochloric acid. The precipitate is filtered off, washed with water, dried and then recrystallized from carbon tetrachloride. M.p. 183°C.

The following compounds are obtained in an analogous manner:

EXAMPLE 5

From N-(2'-chloro-4'-nitrophenyl)-3,5-dichlorosalicylic acid imide chloride there is obtained:
3,5,2'-trichloro-4'-nitro-thionosalicylic acid anilide, m.p. 160°C.

EXAMPLE 6

From N-(2',6'-dichloro-4'-nitrophenyl)-3,5-dichlorosalicylic acid imide chloride there is obtained:
3,5,2',6'-tetrachloro-4'-nitro-thionosalicylic acid anilide, m.p. 182°C.

EXAMPLE 7

From N-(2',3'-dichlorophenyl)-3,5-dichlorosalicylic acid imide chloride there is obtained:
3,5,2',3'-tetrachloro-thionosalicylic acid anilide, m.p. 196°C.

EXAMPLE 8

From N-(3',5'-dichlorophenyl)-3,5-dichlorosalicylic acid imide chloride there is obtained:
3,5,3',5'-tetrachloro-thionosalicylic acid anilide, m.p. 131°C.

EXAMPLE 9

From N-(2',5'-dichlorophenyl)-3,5-dichlorosalicylic acid imide chloride there is obtained: 3,5,2',5'-tetrachloro-thionosalicylic acid anilide, m.p. 196°C.

EXAMPLE 10

From N-(2',3'-dichlorophenyl)-3,5-dibromosalicylic acid imide chloride there is obtained:
3,5-dibromo-2',3'-dichloro-thionosalicylic acid anilide, m.p. 150°C.

EXAMPLE 11

From N-(3',5'-dichlorophenyl)-3,5-dibromosalicylic acid imide chloride there is obtained:
3,5-dibromo-3',5'-dichloro-thionosalicylic acid anilide, m.p. 161°C.

EXAMPLE 12

From N-(4'-chlorophenyl)-5-nitrosalicylic acid imide chloride there is obtained:
   5-nitro-4'-chloro-thionosalicylic acid anilide, m.p. 204°C.

EXAMPLE 13

From N-(4'-chlorophenyl)-3-nitrosalicylic acid imide chloride there is obtained:
   3-nitro-4'-chloro-thionosalicylic acid anilide, m.p. 148°C.

EXAMPLE 14

3,5,2'-trichloro-thionosalicylic acid anilide

30 Grams of N-(2'-chlorophenyl)-6,8-dichloro-2,4-dioxodihydrobenzoxazine-(1,3), prepared from the appropriately substituted salicylic acid anilide in analogy with the process known from Z. Chemie 3 (1963), 148, and Belgian Pat. No. 604,159, are mixed intimately with 19 g of phosphorus pentasulphide and the reaction mixture is heated at 200°C for 30 minutes. The resultant mixture of N-(2'-chlorophenyl)-6,8-dichloro-2-oxo-4-thiono-dihydrobenzoxazine-(1,3) and N-(2'-chlorophenyl)-6,8-dichloro-2,4-dithiono-dihydrobenzoxazine-(1,3) is taken up with 400 ml of boiling dioxan and the dioxan solution is stirred at 80°C into 400 ml of a normal potassium hydroxide solution. The mixture is then heated on a water bath for 1 hour. After cooling, the mixture is filtered and the filtrate acidified with dilute hydrochloric acid. The precipitate is filtered off, washed with water, dried and recrystallized from carbon tetrachloride. M.p. 117°C.

The following compounds are prepared in analogous manner:

EXAMPLE 15

3,5,2',4'-tetrachloro-thionosalicylic acid anilide, m.p. 172°C.

EXAMPLE 16

3,5-dichloro-4'-methoxy-thionosalicylic acid anilide, m.p. 140°C.

EXAMPLE 17

3,5-dichloro-4'-ethoxy-thionosalicylic acid anilide, m.p. 148°C.

EXAMPLE 18

3,5,3'-trichloro-thionosalicylic acid anilide 16.3 Grams (0.1 mole) of 2,4-dichlorophenol and 16.9 g of 3-chlorophenyl-isothiocyanate are mixed, 25 g of finely powdered aluminum chloride are added and the mixture is subsequently heated at 60°C for 24 hours. After cooling, the mixture is decomposed with ice and hydrochloric acid, the supernatant water is decanted and the semi-solid residue is again treated with dilute hydrochloric acid. The mixture is then stirred with a dilute sodium hydroxide solution, filtered and the filtrate is acidified with acetic acid. The precipitate is filtered off, washed with water and recrystallized from 80% alcohol. m.p. 134°C.

The following examples are obtained in analogous manner:

EXAMPLE 19

From 2,4-dichlorophenol and 3,4-dichlorophenyl-isothiocyanate there is obtained:
   3,5,3',4'-tetrachloro-thionosalicylic acid anilide, m.p. 136°C.

EXAMPLE 20

From 3,5-dibromophenol and 4-bromophenyl-isothiocyanate there is obtained:
   3,5,4'-tribromo-thionosalicylic acid anilide, m.p. 132°C.

The following compounds were also obtained in analogy with the method described in Example 4:

EXAMPLE 21

From N-(3'-chloro-4'-methyl-phenyl)-3,5-dichlorosalicylic acid imide chloride:
   3,5,3'-trichloro-4'-methyl-thionosalicylic acid anilide, m.p. 138°C.

EXAMPLE 22

Frm N-(3'-methyl-4'-chloro-phenyl)-3,5-dichlorosalicylic acid imide chloride:
   3,5,4'-trichloro-3'-methyl-thionosalicylic acid anilide, m.p. 127°C.

EXAMPLE 23

From N-(3',4'-dimethyl-phenyl)-3,5-dichlorosalicylic acid imide chloride:
   3,5-dichloro-3',4'-dimethyl-thionosalicylic acid anilide, m.p. 140°C.

EXAMPLE 24

From N-(3',5'-bis-trifluoromethyl-phenyl)-3,5-dichlorosalicylic acid imide chloride:
   3,5-dichloro-3',5'-bis-trifluoromethyl-thionosalicylic acid anilide, m.p. 164°C.

EXAMPLE 25

From N-phenyl-3,5-dichlorosalicylic acid imide chloride: 3,5-dichloro-thionosalicylic acid anilide, m.p. 136°C.

EXAMPLE 26

From N-(4'-chlorophenyl)-3,5-dibromosalicylic acid imide chloride:
   3,5-dibromo-4'-chloro-thionosalicylic acid anilide, m.p. 157°C.

EXAMPLE 27

From N-(2',4'-dichlorophenyl)-3,5-dibromosalicylic acid imide chloride:
   3,5-dibromo-2',4'-dichloro-thionosalicylic acid anilide, m.p. 158°C.

EXAMPLE 28

From N-(3',4'-dichlorophenyl)-3,5-dibromosalicylic acid imide chloride:
   3,5-dibromo-3',4'-dichloro-thionosalicylic acid anilide, m.p. 159°C.

EXAMPLE 29

From N-(2',4',5'-trichlorophenyl)-3,5-dibromosalicylic acid imide chloride:
   3,5-dibromo-2',4',5'-trichloro-thionosalicylic acid anilide, m.p. 178°C.

EXAMPLE 30

From N-(2',4',6'-tribromophenyl)-3,5-dibromosalicylic acid imide chloride:
3,5,2',4',6'-pentabromo-thionosalicylic acid anilide, m.p. 173°C.

EXAMPLE 31

From N-(2',4',6'-trichlorophenyl)-3,5-dibromosalicylic acid imide chloride:
3,5-dibromo-2',4',6'-trichloro-thionosalicylic acid anilide, m.p. 168°C.

EXAMPLE 32

From N-(2',4',6'-tribromophenyl)-3,5-dichlorosalicylic acid imide chloride:
3,5-dichloro-2',4',6'-tribromo-thionosalicylic acid anilide, m.p. 164°C.

EXAMPLE 33

2-acetoxy-3,5-dichloro-N-(4'-chlorophenyl)-thionobenzamide 7.8 Grams (1/10 mole) of acetyl chloride are slowly added dropwise at room temperature to a stirred solution of 33 g (1/10 mole) 3,5,4'-trichloro-thionosalicylic acid anilide and stirring is continued at room temperature for 3½ hours. The precipitate is filtered off with suction, extracted several times with water and redissolved from ethanol. The 2-acetoxy-3,5-dichloro-N-(4'-chlorophenyl)-thionobenzamide melts at 168°C.

In analogy there is obtained from 3,5,4'-tribromo-thionosalicylic anilide and acetylchloride, the compound 2-acetoxy-3,5dibromo-N-(4'-bromophenyl)-thiobenzamide of m.p. 176°C.

EXAMPLE 34

In analogy with Example 33 there is obtained from 3,5,3',4'-tetrachloro-thionosalicylic acid anilide and acetyl chloride, the compound 2-acetoxy-3,5-dichloro-N-(3',4'-dichlorophenyl)-thionobenzamide of m.p. 188°C.

EXAMPLE 35

3,5-dichloro-2'-methyl-4'-chloro-thionosalicylic acid anilide

A solution of 13 g of N-(2'-methyl-4'-chlorophenyl)-3,5-dichlorosalicylic acid imide chloride and 5.7 g of thiourea in 200 ml of anhydrous acetone is heated at boiling temperature for 10 hours. The solvent is then distilled off and the residue is taken up with a boiling 5% sodium carbonate solution. The mixture is then filtered and the filtrate, after cooling, acidified with dilute hydrochloric acid. The precipitate is filtered off, washed with water, dried and recrystallized from ethanol. m.p. 180°C.

EXAMPLE 36

The compound of Example 14 is also obtained in the following manner:

30 g of N-(2'-chlorophenyl)-6,8-dichloro-2-oxo-4-thionodihydrobenzoxazine-(1.3) are taken up in 400 ml of boiling dioxan. The boiling solution is stirred into 400 ml of N KOH warmed to about 80°C, and thereafter is heated for about 1 more hour on the waterbath. After cooling it is filtered and the filtrate acidified with dilute HCl. The precipitate is filtered off, washed with water, dried and recrystallized from carbon tetrachloride. m.p. 117°C.

The following compounds are similarly prepared:
From N-(2',4'-dichlorophenyl)-6,8-dichloro-2-oxo-4-thionodihydro-benzoxazine-(1,3):
3,5,2',4'-tetrachloro-thionosalicylic acid anilide, m.p. 172°C.
From N-(4'-methoxyphenyl)-6,8-dichloro-2-oxo-4-thionodihydro-benzoxazine-(1,3):
3,5-dichloro-4'-methoxy-thionosalicylic acid anilide, m.p. 140°C.
From N-(4'-ethoxyphenyl)-6,8-dichloro-2-oxo-4-thionodihydro-benzoxazine-(1,3):
3,5-dichloro-4'-ethoxy-thionosalicylic acid anilide, m.p. 148°C.
From N-(2',5'-dichlorophenyl)-6,8-dichloro-2-oxo-4-thionodihydro-benzoxazine-(1,3):
3,5,2',5'-tetrachloro-thionosalicylic acid anilide, m.pt. 196°C.
From N-(4'-chlorophenyl)-6,8-dichloro-2-oxo-thiono-dihydrobenzoxazine-(1,3):
3,5,4'-trichloro-thionosalicylic acid anilide, m.pt. 142°C.
From N-(2',4',5'-trichlorophenyl)-6,8-dichloro-2-oxo-4-thiono-dihydro-benzoxazine-(1,3):
3,5,2',4',5'-pentachloro-thionosalicylic acid anilide, m.pt. 183°C.
From N-(3',4'-dichlorophenyl)-6,8-dichloro-2-oxo-4-thionodihydro-benzoxazine-(1,3):
3,5,3',4'-tetrachloro-thionosalicylic acid anilide, m.pt. 136°C.
From N-(4'-chlorophenyl)-6,8-dichloro-2,4-dithio-dihydrobenzoxazine-(1,3):
3,5,4'-trichloro-thiono-salicylic acid anilide. M.pt. 142°C.
From N-(2'-methyl-4'-chlorophenyl)-6,8-dichloro-2,4-dithiodihydrobenzoxazine-(1,3):
3,5,4'-trichloro-2'-methyl-thiono-salicylic acid anilide, m.pt. 180°C.
From N-(3',4'-dichlorophenyl)-6,8-dichloro-2,4-dithio-dihydrobenzoxazine-(1,3):
3,5,3',4'-tetrachloro-thiono-salicylic acid anilide. M.pt. 136°C.
From N-(4'-bromophenyl)-6-chloro-8-bromo-2,4-dithio-dihydrobenzoxazine-(1,3):
3,4'-dibromo-5-chloro-thiono-salicylic acid anilide, m.pt. 154°C.
From N-(3',5'-bis-trifluoromethyl-phenyl)-6,8-dichloro-2,4-dithio-dihydrobenzoxazine-(1,3):
3,5-dichloro-3',5'-bis-trifluoromethyl-thiono-salicylic acid anilide. m.p. 164°C.
From N-(4'-bromophenyl)-6,8-dichloro-2-oxo-4-thio-dihydrobenzoxazine-(1,3):
3,5-dichloro-4'-bromo-thionosalicylic acid anilide. m.p. 164° to 165°C.
From N-(3',5'-bis-trifluoromethyl-phenyl)-6,8-dichloro-2-oxo-4-thio-dihydrobenzoxazine-(1,3):
3,5-dichloro-3',5'-bis-trifluoromethyl-thiono-salicylic acid anilide. m.p. 164°C.
From N-(2'-methyl-4'-chlorophenyl)-6,8-dichloro-2-oxo-4-thio-dihydrobenzoxazine-(1,3):
3,5,4'-trichloro-2'-methyl-thiono-salicylic acid anilide. m.p. 180°C.
From N-(3',5'-bis-fluoromethyl-phenyl)-6,8-dibromo-2-oxo-4-thio-dihydrobenzoxazine-(1,3):
3,5-dibromo-3',5'-bis-trifluoromethyl-thiono-salicylic acid anilide. m.p. 155°C.

From N-(4'-chlorophenyl)-6,8-dibromo-2-oxo-4-thio-dihydrobenzoxazine-(1,3):

3,5-dibromo-4'-chloro-thiono-salicylic acid anilide. m.p. 157°C.

From N-(4'-bromophenyl)-6-chloro-8-bromo-2-oxo-4-thio-dihydrobenzoxazine-(1,3):

3,4'-dibromo-5-chloro-thiono-salicylic acid anilide. m.p. 154°C.

From N-(4'-bromophenyl)-6,8-dibromo-7-methyl-2-oxo-4-thiodihydrobenzoxazine-(1,3):

3,5,4'-tribromo-4-methyl-thiono-salicylic acid anilide. m.p. 144°C.

From N-(3',4'-dichlorophenyl)-6,8-dibromo-7-methyl-2-oxo-4-thio-dihydrobenzoxazine-(1,3):

3,5-dibromo-4-methyl-3',4'-dichloro-thiono-salicylic acid anilide. m.p. 173°C.

From N-(3'-trifluoromethyl-phenyl)-6,8-dichloro-2-oxo-4-thio-dihydrobenzoxazine-(1,3):

3,5-dichloro-3'-trifluoromethyl-thiono-salicylic acid anilide. m.p. 121°C.

From N-(2'-trifluoromethyl-phenyl)-6,8-dichloro-2-oxo-4-thio-dihydrobenzoxazine-(1,3):

3,5-dichloro-2'-trifluoromethyl-thiono-salicylic acid anilide. m.p. 115°C.

EXAMPLE 37

3-[4'-chlorophenyl]-6,8-dichloro-2-oxo-4-thiono-dihydrobenzoxazine-(1,3)

To a suspension of 66.4 g (0.2 mol) of 3,5,4'-trichlorothionosalicylic acid anilide in 200 ml of anhydrous toluol there are added dropwise under stirring at a temperature between 60° and 70°C 20 g of (0.22 mol) oxalylchloride, the resulting solution stirred at boiling temperature for a further 2 hours, the precipitate formed after cooling being suction filtered and recrystallized from dimethylformamide. m.p. 277°C.

The following compounds are similarly prepared:

EXAMPLE 38

From 3,4,2',5'-tetrachloro-thionosalicylic acid anilide and oxalylchloride, the compound 3-[2',5'-dichlorophenyl]-6,8-dichloro-2-oxo-4-thiono-dihydrobenzoxazine-(1,3). m.p. 211°C.

EXAMPLE 39

From 3,5,3',4'-tetrachloro-thionosalicylic acid anilide and oxalylchloride, the compound 3-[3',4'-dichlorophenyl]-6,8-dichloro-2-oxo-4-thiono-dihydrobenzoxazine-(1,3). m.p. 239° C.

EXAMPLE 40

From 3,5,2',4',5'-pentachloro-thionosalicylic acid anilide and oxalylchloride, the compound 3-[2',4',5'-trichlorophenyl]-6,8-dichloro-2-oxo-4-thiono-dihydrobenzoxazine-(1,3). m.p. 203° C.

EXAMPLE 41

3-(3',5'-bis-trifluoromethyl-phenyl)-6,8-dichloro-2-oxo-4-thionodihydrobenzoxazine-(1,3)

To a solution of 43 g (0.1 mol) of 3,5-dichloro-3',5'-bis-trifluoromethyl-thionosalicylic acid anilide in 250 ml of toluol and 7.9 g (0.1 mol) of pyridine is added dropwise under stirring at room temperature 10.8 g (0.1 mol) of chloroformic acid ethyl ester, diluted with 50 ml of toluol, the solution is then stirred at boiling temperature for 2 more hours, thereafter the solvent is distilled off under vacuum and the residue extracted with water and from alcohol. m.p. 190° C.

The following compounds are similarly prepared:

EXAMPLE 42

From 3,5-dibromo-3',5'-bistrifluoromethyl-thionosalicylic acid anilide and chloroformic acid ethyl ester, the compound 3-(3',5'-bis-trifluoromethyl-phenyl)-6,8-dibromo-2-oxo-4-thiono-dihydrobenzoxazine-(1,3). m.p. 210°C.

EXAMPLE 43

From 3,5,4'-trichloro-2'-methyl-thionosalicylic acid anilide and chloroformic acid ethyl ester, the compound 3-(2'-methyl-4'-chlorophenyl)-6,8-dichloro-2-oxo-4-thiono-dihydrobenzoxazine-(1,3). m.p. 240°C.

EXAMPLE 44

From 3,5-dibromo-4'-chloro-thionosalicylic acid anilide and chloroformic acid methyl ester, the compound 3-(4'-chlorophenyl)-6,8-dibromo-2-oxo-4-thiono-dihydrobenzoxazine-(1,3). m.p. 314°C.

EXAMPLE 45

From 3,4'-dibromo-5-chloro-thionosalicylic acid anilide, the compound 3-(4'-bromophenyl)-6-chloro-8-bromo-2-oxo-4-thiono-dihydrobenzoxazine-(1,3). m.p. 299°C.

EXAMPLE 46

From 3,5,4'-tribromo-4-methyl-thionosalicylic acid anilide and chloroformic acid methyl ester, the compound 3-(4'-bromophenyl)-6,8-dibromo-7-methyl-2-oxo-4-thiono-dihydrobenzoxazine-(1,3). m.p. 281°C.

EXAMPLE 47

From 3,5-dibromo-4-methyl-3',4'-dichloro-thionosalicylic acid anilide and chloroformic acid methyl ester, the compound 3-(3',4'-dichlorophenyl)-6,8-dibromo-7-methyl-2-oxo-4-thiono-dihydrobenzoxazine-(1,3). m.p. 284°C.

EXAMPLE 48

From 3,5-dichloro-3'-trifluoromethyl-thionosalicylic acid anilide and chloroformic acid methyl ester, the compound 3-(3'-trifluoromethyl-phenyl)-6,8-dichloro-2-oxo-4-thiono-dihydrobenzoxazine-(1,3). m.p. 215°C.

EXAMPLE 49

From 3,5-dichloro-2'-trifluoromethyl-thionosalicylic acid anilide and chloroformic acid methyl ester, the compound 3-(2'-trifluoromethyl-phenyl)-6,8-dichloro-2-oxo-4-thiono-dihydrobenzoxazine-(1,3). m.p. 175°C.

EXAMPLE 50

In similar manner to Example 41, the compound 3-(4'-bromophenyl)-6,8-dichloro-2-oxo-4-thiono-dihydrobenzoxazine-(1,3) is prepared from 3,5-dichloro-4'-bromo-thiosalicylic acid anilide and chloroformic acid methyl ester. m.p. 286°–287°C.

EXAMPLE 51

3-(4'-chlorophenyl)-6,8-dichloro-2,4-dithiono-dihydrobenzoxazine-(1,3). m.p. 184°C.

To a stirred suspension of 32.2 g (0.1 mol) of 3,5,4'-trichloro-thionosalicylic acid anilide in 250 ml of anhydrous toluol, 20.2 g (0.2 mol) of triethylamine are added and, after a clear solution has gradually formed transiently, 11.5 g (0.1 mol) of thiophosgene, diluted with some anhydrous toluol, is slowly added dropwise after the precipitation of the triethylamine salt at room temperature. Thereupon it is stirred for another 20 hours at room temperature, briefly heated to the boil, suction filtered hot from insolubles, the filtrate cooled and the precipitate which falls out dissolved and allowed to crystallize from chlorobenzol.

EXAMPLE 52

Similarly to Example 51, there was obtained from 3,5,4'-trichloro-2'-methyl-thionosalicylic acid anilide and thiophosgene the compound 3-(2'-methyl-4'-chlorophenyl)-6,8-dichloro-2,4-dithio-dihydrobenzoxazine-(1,3). Therein it is advantageous in connection with the 20 hour after-stirring at room temperature that the suction filtering be carried out cold and the volume of the filtrate be reduced one-half under vacuum. Upon crystallization from toluol the compound melted at 190°C.

EXAMPLE 53

Similarly to Example 52, there was obtained from 3,4'-dibromo-5-chloro-thionosalicylic acid anilide and thiophosgene the compound 3-(4'-bromophenyl)-6-chloro-8-bromo-2,4-dithio-dihydrobenzoxazine-(1,3). Upon cooling of the filtrate no appreciable amount of precipitate forms and like Example 52 the volume of the filtrate is reduced under vacuum. Crystallized from toluol. m.p. 191°C.

EXAMPLE 54

Similarly to Example 52, there is obtained from 3,5,3',4'-tetrachloro-thionosalicylic acid anilide and thiophosgene the compound 3-(3',4'-dichlorophenyl)-6,8-dichloro-2,4-dithio-dihydrobenzoxazine-(1,3). On account of the better yield it is expedient that the residue in the filter be stirred with cold water and the insoluble part combined with the portion gained from the filtrate. Crystallized from toluol. m.p. 180°C.

EXAMPLE 55

Similarly to Example 51, 43.4 g (0.1 mol) of 3,5-dichloro3',5'-bis-trifluoromethyl-thionosalicylic acid anilide were suspended in 300 ml of anhydrous toluol and, under stirring after the addition of 0.2 mol of triethylamine and 0.1 mol thiophosgene, heated to boiling under reflux for 20 hours. Thereafter it is suction filtered hot, the filtrate evaporated to dryness under vacuum and the remaining residue of the 3-(3',5'-bis-trifluoromethylphenyl)-6,8-dichloro-2,4-dithio-dihydrobenzoxazine-(1,3) crystallized from cyclohexane. m.p. 152°C.

EXAMPLE 56

3-(4'-bromophenyl)-6-chloro-8bromo-2-oxo-4-thio-dihydrobenzoxazine-(1,3).

To a stirred suspension of 42.1 g (0.1 mol) of 3,4'-dibromo-5-chloro-thionosalicylic acid anilide in 300 ml of anhydrous toluol were added at room temperature 20.2 g (0.2 mol) of triethylamine and after coming down - the triethylamine salt from the previously standing clear solution 10 g (0.1 mol) of phosgene dissolved in 50 ml of anhydrous toluol- is added dropwise. After 20 hours stirring at room temperature it is heated briefly to the boil, suction filtered hot from insolubles and the precipitate deposited by the cooling of the filtrate crystallized from chlorobenzol. m.p. 299°C.

EXAMPLE 57

Similarly to Example 56, there is obtained from 3,5,4'-trichloro-thionosalicylic acid anilide and phosgene in the presence of triethylamine the compound 3-(4'-chlorophenyl)-6,8-dichloro-2-oxo-4-thio-dihydrobenzoxazine-(1,3). m.p. 277°C.

EXAMPLE 58

From N-(2'-methylmercapto-4'-chloro-5'-methylphenyl)-3,5-dichloro-salicylic acid imide chloride: the compound 3,5,4'-trichloro-2'-methylmercapto-5'-methyl-thionosalicylic acid anilide, m.p. 181°C.

EXAMPLE 59

From N-(2'-methylmercapto-4',5'-dichlorophenyl)-3,5-dichlorosalicylic acid imide chloride: the compound 3,5,4',5'-tetrachloro-2'-methylmercapto-thionosalicylic acid anilide: m.p. 205°C.

EXAMPLE 60

From N-(3'-trifluoromethyl-phenyl)-3,5-dichlorosalicylic acid imide chloride: the compound 3,5-dichloro-3'-trifluoromethylthionosalicylic acid anilide. m.p. 121°C.

EXAMPLE 61

From N-(4'-bromophenyl)-3-bromo-5-chloro-salicylic acid imide chloride: the compound 3,4'-dibromo-5-chloro-thionosalicylic acid anilide. m.p. 154°C.

EXAMPLE 62

From N-(2'-trifluoromethyl-phenyl)-3,5-dichlorosalicylic acid imide chloride: the compound 3,5-dichloro-2'-trifluoromethylthionosalicylic acid anilide. m.p. 115°C.

EXAMPLE 63

From N-(2'-trifluoromethyl-4'-bromophenyl)-3,5-dichlorosalicylic acid imide chloride: the compound 3,5-dichloro-2'-trifluoromethyl-4'-bromo-thionosalicylic acid anilide. m.p. 164°C.

EXAMPLE 64

From N-(3',5'-bis-trifluoromethyl-phenyl)-3,5-dibromosalicylic acid imide chloride: the compound 3,5-dibromo-3',5'-bis-trifluoromethyl-thionosalicylic acid anilide. m.p. 155°C.

EXAMPLE 65

From N-(4'-bromophenyl)-3,5-dibromo-4-methylsalicylic acid imide chloride: the compound 3,5,4'-tribromo-4-methyl-thionosalicylic acid anilide. m.p. 144°C.

EXAMPLE 66

From N-(3',4'-dichlorophenyl)-3,5-dibromo-4-methylsalicylic acid imide chloride: the compound 3,5-dibromo-4-methyl-3',4'-dichloro-thionosalicylic acid anilide. m.p. 173°C.

EXAMPLE 67

From N-(3',4'-dichlorophenyl)-3-nitro-salicylic acid imide chloride: the compound 3-nitro-3',4'-dichloro-thionosalicylic acid anilie. m.p. 149°C.

EXAMPLE 68

From N-(2',4',5'-trichlorophenyl)-3-nitro-salicylic acid imide chloride: the compound 3-nitro-2',4',5'-trichloro-thionosalicylic acid anilide. m.p. 191°C.

EXAMPLE 69

From N-(2'-methyl-4'-chlorophenyl)-3-nitro-salicylic acid imide chloride: the compound 3-nitro-2'-methyl-4'-chloro-thionosalicylic acid anilide. m.p. 174°C.

EXAMPLE 70

Similarly to Example 33 there is obtained from 3,5-dichloro-3',5'-bis-trifluoromethyl-thionosalicylic acid anilide and acetylchloride the compound 2-acetoxy-3,5-dichloro-N-(3',5'-bis-trifluoromethyl-phenyl)-thionobenzamide. m.p. 129°C.

EXAMPLE 71

From 3,4'-dibromo-5-chloro-thionosalicylic acid anilide and acetylchloride the compound 2-acetoxy-3-bromo-5-chloro-N-(4'-bromophenyl)-thionobenzamide. m.p. 181°C.

EXAMPLE 72

From 3,5-dibromo-3',5'-bis-trifluoromethyl-thionosalicylic acid anilide and acetylchloride the compound 2-acetoxy-3,5-dibromo-N-(3',5'-bis-trifluoromethyl-phenyl)-thionobenzamide. m.p. 139°C.

EXAMPLE 73

3,5-dichloro-4'-bromo-thionosalicylic acid anilide 95 g (0.25 mol) of N-(4'-bromophenyl)-3,5-dichloro-salicylic acid imide chloride and 30 g (0.3 mol) of sodium thioacetate were heated to boiling in 250 ml of dry acetone for 12 hours under stirring and reflux. Thereafter it was filtered, distilled under vacuum and the residue warmed with 1200 ml of a 1N aqueous KOH solution for ½ hour on the steambath. After cooling it was filtered, the clear filtrate adjusted with dilute Congo acid and the precipitated reaction product crystallized from toluol. m.p. 164° to 165°C.

EXAMPLE 74

3,5,4'-trichloro-3'-hydroxy-thionosalicylic acid anilide 98 g (0.25 mol) of N-(3'-acetoxy-4'-chlorophenyl)-3,5-dichloro-salicylic acid imide chloride and 48 g (0.3 mol) of potassium ethyl xanthogenate were heated to boiling in 1000 ml of dry acetone for 15 hours under stirred reflux. Thereafter it is filtered, the solvent distilled off under vacuum, the solution of the residue in 500 ml of dioxan stirred into 1000 ml of a 1N aqueous KOH solution heated to 80° C and the temperature held a further ½ hour at 80° C. After filtration and upon the addition of dilute HCL until reaction with Congo acid, the reaction product separates out in the form of a dark brown oil, which desirably is immediately taken up in ether. By boiling out of the evaporation residue of the ethereal solution with excess 10% aqueous soda solution, the reaction product can be recovered with a reduced amount of oily impurity so that upon acidification of the clarified soda solution over charcoal the desired product no longer separates out in crystalline form. Crystallization from toluol yields yellow colored crystals of m.p. 168° C.

EXAMPLE 75

Similarly to Example 74, there is obtained from N-(2'-chloro-4'-acetoxy-phenyl)-3,5-dichlorosalicylic acid imide chloride the compound 3,5,2'-trichloro-4'-hydroxy-thionosalicylic acid anilide.

EXAMPLE 76

Similarly to Example 33, there is obtained from 3,5,4'-trichloro-2'-methyl-thionosalicylic acid anilide and acetylchloride the compound 2-acetoxy-3,5-dichloro-N-(2'-methyl-4'-chlorophenyl)-thionobenzamide. m.p. 180°C.

EXAMPLE 77

From 3,4'-dibromo-5-chloro-thionosalicylic acid anilide and β-phenylpropionylchloride there is obtained the compound 2-β-phenylpropionyloxy-3-bromo-5-chloro-N-(4'-bromo-phenyl)-thionobenzamide. m.p. 146°C.

EXAMPLE 78

From 3,4'-dibromo-5-chloro-thionosalicylic acid anilide and lauroylchloride there is obtained the compound 2-lauroyloxy-3-bromo-5-chloro-N-(4'-bromophenyl)-thionobenzamide. m.p. 100°C.

EXAMPLE 79

From 3,4'-dibromo-5-chloro-thionosalicylic acid anilide and pivaloylchloride there is obtained the compound 2-pivaloyloxy-3-bromo-5-chloro-N-(4'-bromophenyl)-thionobenzamide. m.p. 180°C.

EXAMPLE 80

From 3,4'-dibromo-5-chloro-thionosalicylic acid anilide and methanesulfonic acid chloride there is obtained the compound 2-methanesulfonyloxy-3-bromo-5-chloro-N-(4'-bromo-phenyl)-thionobenzamide. m.p. 206°C.

EXAMPLE 81

To a suspension of 33.2 g (0.1 mol) of 3,5,4'-trichlorothionosalicylic acid anilide and 1 g of sodium methylate in 200 ml of dry toluol there were added dropwise under stirring at room temperature 7.1 g (0.1 mol) of ethylisocyanate diluted with a little dry toluol and the whole thereafter heated for 8 hours under reflux. After cooling it is suction filtered and the 2-(N'-ethyl-carbaminoyloxy)-3,5-dichloro-N-(4'-chlorophenyl)-thionobenzamide is crystallized from toluol. m.p. 163°C with decomposition.

EXAMPLE 82

Similarly to Example 81, there is obtained from 3,4'-dibromo-5-chloro-thionosalicylic acid anilide and ethylisocyanate the compound 2-(N'-ethyl-carbaminoyloxy)-3-bromo-5-chloro-N-(4'-bromophenyl)-thionobenzamide. m.p. 165° with decomposition.

What is claimed is:

1. A veterinary composition having parasiticidal activity, which comprises a parasiticidally effective amount of a compound of the formula:

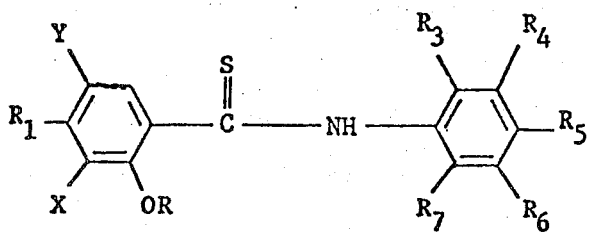

wherein

R is hydrogen, lower alkanoyl or phenyl lower alkanoyl, $R_1$ is hydrogen or lower alkyl, $R_3$, $R_4$, $R_5$, $R_6$ and $R_7$ are the same or different and are each hydrogen, lower alkyl, lower alkoxy, halogen, nitro, trifluoromethyl or lower alkylmercapto and X and Y are the same or different, wherein X is halogen or nitro, and Y is hydrogen or halogen, or a salt thereof with a non-toxic inorganic or organic base in combination with a non-toxic veterinary carrier.

2. The composition of claim 1 in which the compound is 3,5,4'-trichlorothionosalicylic acid anilide.

3. The composition of claim 1 in which the compound is 3,5,2',4',5'-pentachloro-thionosalicylic acid anilide.

4. The composition of claim 1 in which the compound is 3,5,2',5'-tetrachloro-thionosalicylic acid anilide.

5. The composition of claim 1 in which the compound is 3,5-dibromo-2',3'-dichloro-thionosalicylic acid anilide.

6. The composition of claim 1 in which the compound is 3,5-dibromo-3',5'-dichloro-thionosalicylic acid anilide.

7. The composition of claim 1 in which the compound is 3-nitro-4'-chlorothionosalicylic acid anilide.

8. The composition of claim 1 in which the compound is 3,5,2',4'-tetrachloro-thionosalicylic acid anilide.

9. The composition of claim 1 in which the compound is 3,5,3',4'-tetrachloro-thionosalicylic acid anilide.

10. The composition of claim 1 in which the compound is 3,5,4'-tribromothionosalicylic acid anilide.

11. The composition of claim 1 in which the compound is 3,5,3'-trichloro-4'-methyl-thionosalicylic acid anilide.

12. The composition of claim 1 in which the compound is 3,5-dibromo-4'-chloro-thionosalicylic acid anilide.

13. The composition of claim 1 in which the compound is 3,5-dichloro-2'-methyl-4'-chloro-thionosalicylic acid anilide.

14. The composition of claim 1 in which the compound is 3,5,4',5'-tetrachloro-2'-methylmercapto-thionosalicylic acid anilide.

15. The composition of claim 1 in which the compound is 3,5,4'-tribromo-4-methyl-thionosalicylic acid anilide.

16. The composition of claim 1 in which the compound is 3,5-dichloro-4'-bromo-thionosalicylic acid anilide.

17. The composition of claim 1 in which the compound is 2-acetoxy-3,5-dichloro-N-(4'-chlorophenyl)-thionobenzamide.

18. The composition of claim 1 in which the compound is 2-acetoxy-3,5-dichloro-N-(3',4'-dichlorophenyl)-thionobenzamide.

19. The composition of claim 1 in which the compound is 2-acetoxy-3-bromo-5-chloro-N-(4'-bromophenyl)-thionobenzamide.

20. The composition of claim 1 in which the compound is 2-acetoxy-3,5-dichloro-N-(2'-methyl-4'-chlorophenyl)-thionobenzamide.

21. The composition of claim 1 in which the compound is 2-β-phenylpropionyloxy-3-bromo-5-chloro-N-(4'-bromophenyl)-thionobenzamide.

22. The composition of claim 1 in which the compound is 2-pivaloyloxy-3-bromo-5-chloro-N-(4'-bromophenyl)-thionobenzamide.

23. The composition of claim 1, in which the compound has the formula:

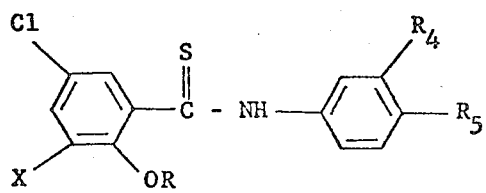

wherein R is hydrogen or acetyl, $R_4$ is hydrogen or chloro, $R_5$ is chloro or bromo, and X is chloro or bromo.

24. The composition of claim 1, in which the compound is 3,5,2'-trichloro-4'-nitro-thionosalicylic acid anilide.

25. The composition of claim 1, in which the compound is 3,5,2',3'-tetrachloro-thionosalicylic acid anilide.

26. The composition of claim 1, in which the compound is 3,5,3',5'-tetrachloro-thionosalicylic acid anilide.

27. A method of treating domestic animals for liver flukes which comprises administering to a domestic animal in need thereof a parasiticidally effective amount of a compound of the formula:

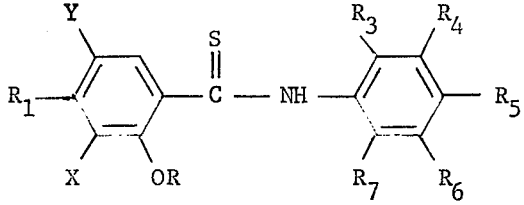

wherein

R is hydrogen, lower alkanoyl or phenyl lower alkanoyl, $R_1$ is hydrogen or lower alkyl, $R_3$, $R_4$, $R_5$, $R_6$ and $R_7$ are the same or different and are each hydrogen, lower alkyl, lower alkoxy, halogen, nitro, trifluoromethyl or lower alkylmercapto and X and Y are the same or different, wherein X is halogen or nitro, and Y is hydrogen or halogen, or a salt thereof with a non-toxic inorganic or organic base.

28. The method of claim 27 in which the compound is 3,5,4'-trichloro-thionosalicylic acid anilide.
29. The method of claim 27 in which the compound is 3,5,2',4',5'-pentachloro-thionosalicylic acid anilide.
30. The method of claim 27 in which the compound is 3,5,2',5'-tetrachloro-thionosalicylic acid anilide.
31. The method of claim 27 in which the compound is 3,5-dibromo-2',3'-dichloro-thionosalicylic acid anilide.
32. The method of claim 27 in which the compound is 3,5-dibromo-3',5'-dichloro-thionosalicylic acid anilide.
33. The method of claim 27 in which the compound is 3-nitro-4'-chloro-thionosalicylic acid anilide.
34. The method of claim 27 in which the compound is 3,5,2',4'tetrachloro-thionosalicylic acid anilide.
35. The method of claim 27 in which the compound is 3,5,3',4'-tetrachloro-thionosalicylic acid anilide.
36. The method of claim 27 in which the compound is 3,5,4'-tribromo-thionosalicylic acid anilide.
37. The method of claim 27 in which the compound is 3,5,3'-trichloro-4'-methyl-thionosalicylic acid anilide.
38. The method of claim 27 in which the compound is 3,5-dibromo-4'-chloro-thionosalicylic acid anilide.
39. The method of claim 27 in which the compound is 3,5-dichloro-2'-chloro-thionosalicylic acid anilide.
40. The method of claim 27 in which the compound is 3,5,4',5'-tetrachloro-2'-methylmercapto-thionosalicylic acid anilide.
41. The method of claim 27 in which the compound is 3,5,4'-tribromo-4-methyl-thionosalicylic acid anilide.
42. The method of claim 27 in which the compound is 3,5-dichloro-4'-bromo-thionosalicylic acid anilide.
43. The method of claim 27 in which the compound is 2-acetoxy-3,5-dichloro-N-(4'-chlorophenyl)-thionobenzamide.
44. The method of claim 27 in which the compound is 2-acetoxy-3,5-dichloro-N-(3',4'-dichlorophenyl)-thionobenzamide.
45. The method of claim 27 in which the compound is 2-acetoxy-3-bromo-5-chloro-N-(4'-bromophenyl)-thionobenzamide.
46. The method of claim 27 in which the compound is 2-acetoxy-3,5-dichloro-N-(2'-methyl-4'-chlorophenyl)-thionobenzamide.
47. The method of claim 27 in which the compound is 2-β-phenylpropionyloxy-3-bromo-5-chloro-N-(4'-bromophenyl)-thionobenzamide.
48. The method of claim 27 in which the compound is 2-pivaloyloxy-3-bromo-5-chloro-N-(4'-bromophenyl)-thionobenzamide.
49. The method of claim 27 in which the compound has the formula:

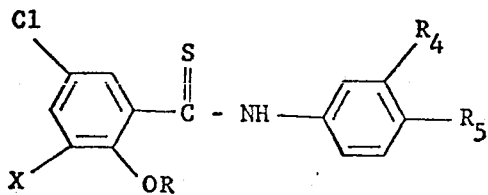

wherein R is hydrogen or acetyl,
$R_4$ is hydrogen or chloro,
$R_5$ is chloro or bromo, and
X is chloro or bromo.
50. The method of claim 27 in which the compound is 3,5,2'-trichloro-4'-nitro-thionosalicylic acid anilide.
51. The method of claim 27 in which the compound is 3,5,2',3'-tetrachloro-thionosalicylic acid anilide.
52. The method of claim 27 in which the compound is 3,5,3',5'-tetrachloro-thionosalicylic acid anilide.

* * * * *